US010640721B2

(12) United States Patent
Sandberg et al.

(10) Patent No.: US 10,640,721 B2
(45) Date of Patent: May 5, 2020

(54) METHOD FOR PRODUCING RENEWABLE MIDDLE-DISTILLATE COMPOSITION, USE OF THE COMPOSITION AND FUEL CONTAINING THE SAME

(71) Applicant: NESTE OYJ, Espoo (FI)

(72) Inventors: Kati Sandberg, Järvenpää (FI); Ulla Kiiski, Hamari (FI); Marina Lindblad, Helsinki (FI); Jukka Myllyoja, Vantaa (FI)

(73) Assignee: NESTE OYJ, Espoo (FI)

( * ) Notice: Subject to any disclaimer, the term of this patent is extended or adjusted under 35 U.S.C. 154(b) by 0 days.

(21) Appl. No.: 15/392,849

(22) Filed: Dec. 28, 2016

(65) Prior Publication Data
US 2017/0183593 A1    Jun. 29, 2017

(30) Foreign Application Priority Data
Dec. 29, 2015    (EP) .................................... 15202931

(51) Int. Cl.
C10L 10/14        (2006.01)
B01J 35/06        (2006.01)
(Continued)

(52) U.S. Cl.
CPC .............. C10L 10/14 (2013.01); B01J 23/44 (2013.01); B01J 35/065 (2013.01); C07C 51/353 (2013.01); C10G 3/46 (2013.01); C10G 3/50 (2013.01); C10L 1/04 (2013.01); C10L 1/08 (2013.01); C10L 10/08 (2013.01);
(Continued)

(58) Field of Classification Search
CPC .... C10L 10/14; C10L 1/04; C10L 1/08; C10L 2270/04; C10L 2290/543; C10L 2270/026; C10L 2200/0446; C10L 2200/0469; C10L 10/08; C07C 51/353; C07C 13/45; C07C 13/10; C07C 9/16; C10G 3/46; C10G 3/50; C10G 2400/04; C10G 2300/202; C10G 2400/02; C10G 50/00; C10G 3/47;
(Continued)

(56) References Cited

U.S. PATENT DOCUMENTS

2006/0135793 A1    6/2006   Blessing et al.
2006/0162239 A1    7/2006   Van Den Brink et al.
(Continued)

FOREIGN PATENT DOCUMENTS

EP           2 924 097 A2       9/2015
WO    WO 2006/067171 A          6/2006
(Continued)

OTHER PUBLICATIONS

European Search Report dated May 30, 2016 for application No. 15202932.8.
(Continued)

Primary Examiner — Pamela H Weiss
(74) Attorney, Agent, or Firm — Buchanan Ingersoll & Rooney PC

(57) ABSTRACT

The present invention provides a fuel comprising a renewable middle distillate composition obtainable by hydrodeoxygenation of a feedstock comprising levulinic acid dimers/oligomers and fractionated distillation. The renewable middle distillate composition contains less than 10.0 wt.-% aromatics.

10 Claims, 1 Drawing Sheet

(51) Int. Cl.
*B01J 23/44* (2006.01)
*C10L 10/08* (2006.01)
*C10L 1/04* (2006.01)
*C10L 1/08* (2006.01)
*C10G 3/00* (2006.01)
*C07C 51/353* (2006.01)

(52) U.S. Cl.
CPC ... *C10G 2300/202* (2013.01); *C10G 2400/04* (2013.01); *C10L 2200/0446* (2013.01); *C10L 2200/0469* (2013.01); *C10L 2270/026* (2013.01); *C10L 2270/04* (2013.01); *C10L 2290/543* (2013.01); *Y02E 50/13* (2013.01); *Y02P 30/20* (2015.11); *Y02T 50/678* (2013.01)

(58) Field of Classification Search
CPC .. C10G 3/45; C10G 3/44; B01J 35/065; B01J 23/44; Y02P 30/20; Y02E 50/13; Y02T 50/678
USPC .................................. 585/1, 14, 16, 240–242
See application file for complete search history.

(56) References Cited

U.S. PATENT DOCUMENTS

| | | | | |
|---|---|---|---|---|
| 2007/0131579 | A1* | 6/2007 | Koivusalmi | ......... C10M 107/10 208/19 |
| 2011/0277378 | A1 | 11/2011 | Von Hebel et al. | |
| 2012/0283493 | A1 | 11/2012 | Olson et al. | |
| 2013/0102817 | A1* | 4/2013 | Dahlstrom | ................ C10L 1/04 585/13 |
| 2013/0144098 | A1* | 6/2013 | Pansare | ..................... C10L 1/04 585/310 |
| 2013/0237728 | A1* | 9/2013 | Lotero | ..................... C10L 1/04 585/242 |

FOREIGN PATENT DOCUMENTS

| | | | | |
|---|---|---|---|---|
| WO | WO 2014161736 | A1* | 10/2014 | ............. C10L 1/023 |
| WO | WO 2015/144994 | A1 | 10/2015 | |

OTHER PUBLICATIONS

M. Mascal, et al., "Hydrodeoxygenation of the Angelica Lactone Dimer, a Cellulose-Based Feedstock: Simple, High-Yield Synthesis of Branched C7-C10 Gasoline-like Hydrocarbons", Angewandte Chemie International Edition, Feb. 10, 2014, pp. 1854-1857, vol. 53, No. 7, XP055260582.

Office Action (Communication) dated Jul. 1, 2019, by the European Patent Office in corresponding European Patent Application No. 15202931.0. (6 pages).

* cited by examiner

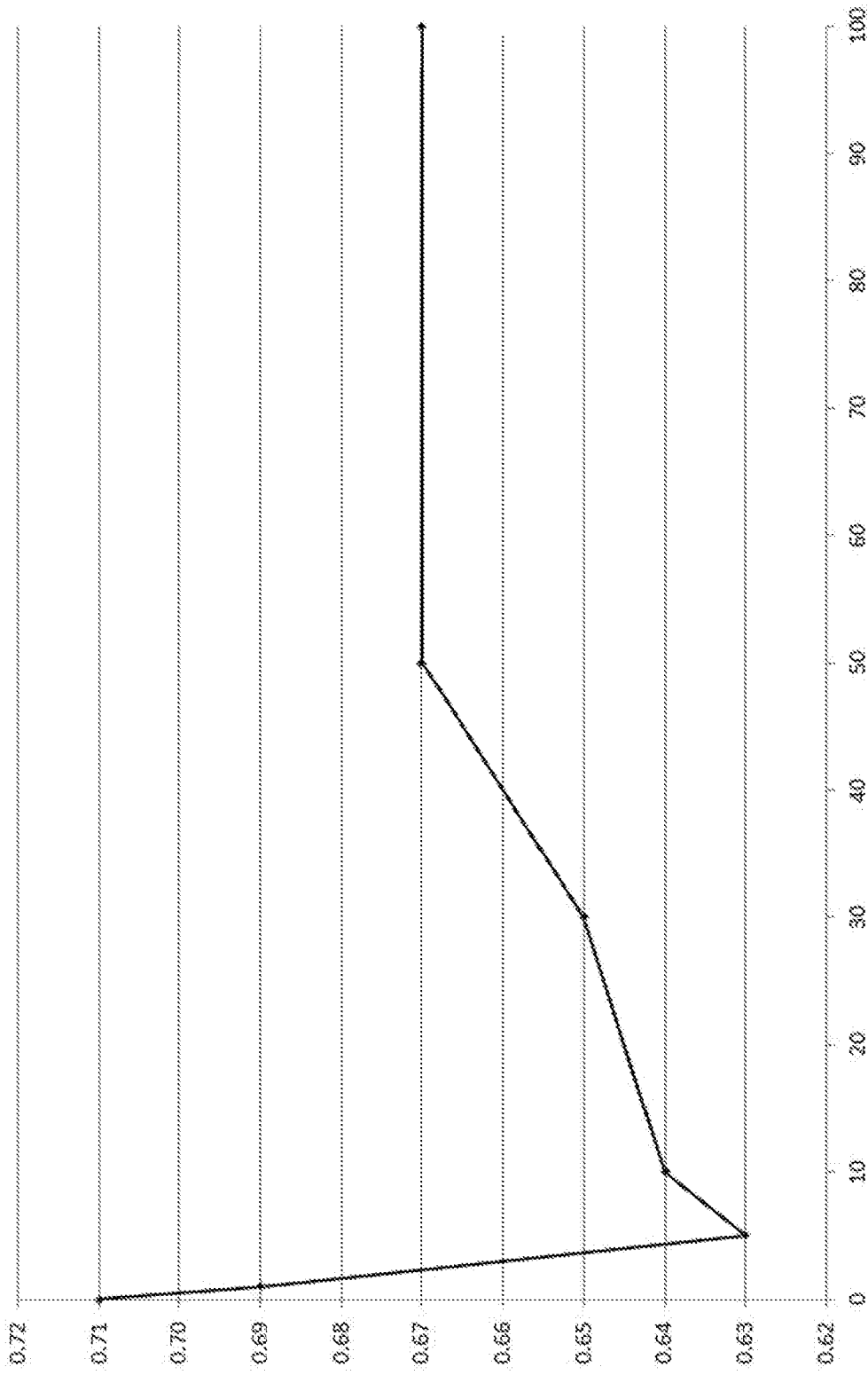

METHOD FOR PRODUCING RENEWABLE MIDDLE-DISTILLATE COMPOSITION, USE OF THE COMPOSITION AND FUEL CONTAINING THE SAME

TECHNICAL FIELD

The present invention relates to a method for producing a renewable middle-distillate hydrocarbon composition, use of the composition and fuel containing the composition. In particular, the present invention relates to hydrocarbon compositions obtained by hydrotreatment of levulinic acid dimers/oligomers derived from renewable sources for the production of fuel or fuel components, to fuel containing these hydrocarbon compositions and to the use of these hydrocarbon compositions as aviation fuel.

BACKGROUND ART

US 2012/0283493 A1 discloses various methods for treatment of fatty acids and lignocellulosic material, including a hydrodeoxygenation treatment.

WO 2006/067171 A1 discloses conversion of a reactant selected from a lactone, a carboxylic acid having a γ-keto group or its ester to a non-cyclic saturated carboxylic acid or ester, wherein the non-cyclic saturated esters can be used in diesel fuel.

EP 2 924 097 A2 discloses a C—C-coupling reaction of levulinic acid which produces up to 35 wt.-% dimers as well as (higher) oligomers. The product may be subjected to HDO treatment and then fractionated for use e.g. as diesel, aviation or gasoline fuel. The gasoline fraction may contain less than 10 wt.-% aromatics. The diesel fraction, which is a middle distillate fraction, contains at least 30 wt.-% aromatics.

WO 2015/144994 A1 discloses thermal C—C-coupling of levulinic acid which results e.g. in dimers, followed by HDO and optional isomerization. Gasoline, aviation and diesel range fractions may be obtained by fractionation. WO 2015/144994 A1 states that isomerization results in a reduction of cyclic compounds but remains silent regarding contents of aromatics in middle distillate fractions.

DISCLOSURE OF THE INVENTION

The present invention relates to a method for producing a renewable middle-distillate hydrocarbon composition, use of the composition and fuel containing the composition. The composition is particularly suitable as a component in aviation fuel/jet fuel, but may be used in diesel range fuel as well. In particular, the present invention relates to compositions obtained by hydrotreatment of levulinic acid dimers/oligomers derived from renewable sources for the production of fuel or fuel components, to fuel containing these compositions and to the use of these compositions as aviation fuel.

Up to date, there are three ASTM-certified production paths for renewable aviation fuel: Fischer-Tropsch synthesis, hydroprocessing of esters and fatty acids (HEFA) and direct sugar to hydrocarbon (DSHC) conversion. According to a vision of the Ministry of Transport and Communication in Finland, 40% of currently used aviation fuels will be replaced by biokerosine in 2050. This large amount requires alternative sources for the production of renewable aviation fuel, in particular high-quality fuel meeting highest demands.

Accordingly, the production of high-quality aviation fuel from renewable sources which are available in large amounts is still a problem to be solved. Further, the increasing use of blo-diesel poses the problem of finding suitable sources for the production of bio-diesel or bio-diesel additives having desirable fuel characteristics.

These problems are solved by the methods, the products and the use as defined in the appended claims.

Specifically, the present invention provides middle-distillate compositions which can be used as fuel components without further purification due to their low content of undesired components.

BRIEF DESCRIPTION OF THE DRAWINGS

FIG. 1 shows BOCLE lubricity (mm) as a function of the content of renewable middle distillate composition of the present invention in blends with fossil fuel (Ex. 3)

DETAILED DESCRIPTION OF THE INVENTION

The present invention relates to a renewable middle-distillate composition usable as a component of aviation fuel or diesel fuel, which is obtained by hydrotreatment of levulinic acid dimers/oligomers which are obtained from a renewable source.

Specifically, the present invention relates to a fuel comprising the renewable middle distillate composition, wherein the renewable middle distillate composition is obtainable by hydrodeoxygenation (or hydrotreatment) of a feedstock comprising levulinic acid dimers/oligomers, followed by fractionated distillation. The fractionated distillation is carried out so as to obtain the middle distillate fraction from the product obtained after hydrodeoxygenation. The renewable middle distillate composition contains less than 10.0 wt.-% of aromatics, as determined in accordance with ASTM D2425.

The renewable middle distillate composition preferably contains at most 9.5 wt.-%, at most 9.3 wt.-%, at most 9.0 wt.-%, at most 8.0 wt.-%, at most 7.0 wt.-%, at most 6.0 wt.-%, at most 5.0 wt.-%, at most 4.0 wt.-%, or at most 3.0 wt.-% of aromatics, as determined in accordance with ASTM D2425. The present inventors surprisingly found that a middle distillate fraction having very low aromatics content can be produced from levulinic acid dimers/oligomers. Low aromatics content is favourable in view of emissions and combustion characteristics.

Due to the use of the feedstock containing levulinic acid dimers/oligomers, the product distribution is narrow and the product properties can be controlled in a well specified range. Furthermore, the resulting product (i.e. the middle distillate fraction) provides a very low freezing point when used alone or in combination with conventional fuel. Furthermore, the cloud point of diesel fuel is very low as well when employing the middle distillate as an admixture. Thus, high-quality fuel can be produced using lignocellulosic material as a renewable source which is available in large amounts.

In the present invention, the levulinic acid may be employed in acid form or as a derivative selected from the group of esters of levulinic acid and/or lactones of levulinic acid. Accordingly, the levulinic acid dimers/oligomers include all kinds of dimers/oligomers obtained from levulinic acid (free acid form) alone, levulinic acid esters alone, levulinic acid lactones alone and mixed dimers/oligomers of these. In the present invention, the expression "containing levulinic acid dimers/oligomers" means that at least one kind of levulinic acid dimer/oligomer is contained.

The levulinic acid dimer/oligomer further includes all compounds directly obtainable from a levulinic acid dimer/oligomer by other reactions under the conditions of a C—C-coupling reaction or distillation, such as (internal) lactonisation and dehydation and further condensation reactions producing e.g. LA-trimers. Examples of levulinic acid dimers/oligomers according to the invention are shown by the following formulas, using free acid dimers as examples:

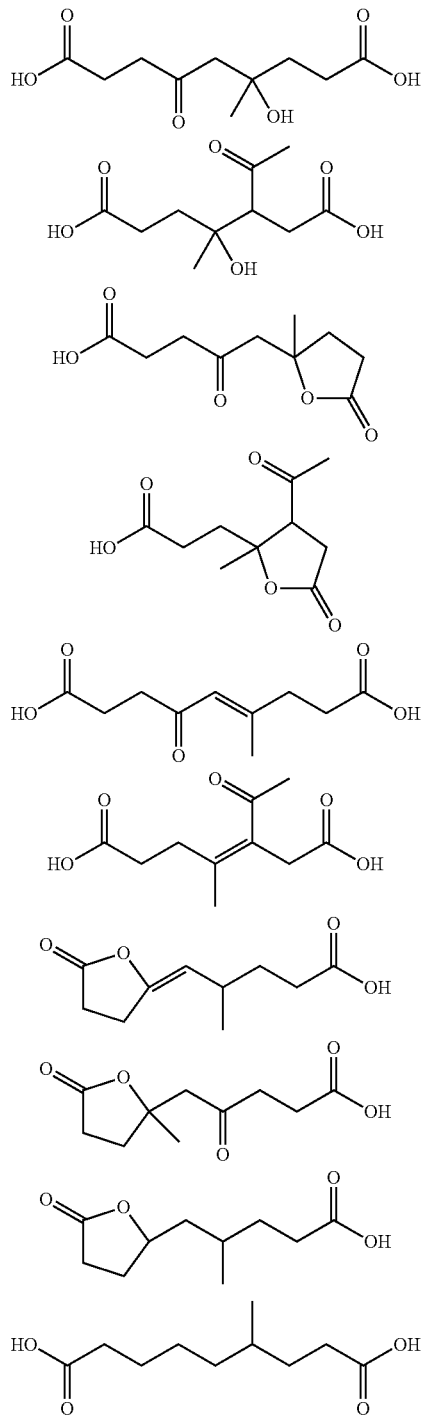

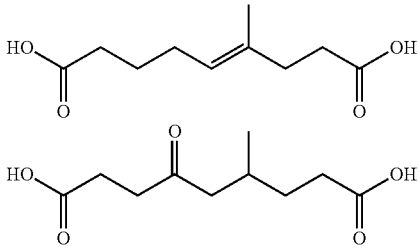

In the present invention, the freezing point of the renewable middle distillate composition is preferably −70° C. or lower. Further, the freezing point of the renewable middle distillate composition may be −80° C. or lower, 10-90° C. or lower, or −95° C. or lower. The freezing point may be determined e.g. in accordance with IP529. The inventors of the present invention surprisingly found that a middle distillate composition obtained form levulinic acid dimers/oligomers provides an extremely low freezing point, which makes it particularly suitable as an aviation fuel component or as a winter diesel component.

In the present invention, the "middle distillate composition" generally relates to the middle distillate fraction contained in the fuel of the present invention, to the middle distillate fraction produced by the process of the present invention and to the middle distillate fraction used in accordance with the present invention. Further, the middle distillate fraction may be a diesel range fraction or an aviation fuel range fraction, and is preferably an aviation fuel range fraction.

Preferably the renewable middle distillate composition contains at least 50 wt.-%, preferably at least 55 wt.-%, more preferably at least 60 wt.-%, or at least 65 wt.-% of cycloparaffins, as determined in accordance with ASTM D2425.

High a content of cycloparaffins surprisingly provides good fuel properties (such as low freezing point and low cloud point) and can be achieved when using levulinic acid dimers/oligomers as a feedstock material by appropriately adjusting the HDO conditions.

The renewable middle distillate composition suitably contains at most 80 wt.-%, preferably at most 75 wt.-%, more preferably at most 72 wt.-%, or at most 70 wt.-% of cycloparaffins, as determined in accordance with ASTM D2425. In general, paraffin hydrocarbons offer the most desirable combustion cleanliness characteristics for jet fuels and diesel fuels. Cycloparaffins are the next most desirable hydrocarbons for this use.

Although the content of the middle distillate fraction in the fuel of the present invention is not particularly limited and may be in the range of 0.01 wt.-% to 100 wt.-% (neat middle distillate fraction), in view of adjusting the fuel properties (such as density, lubricity, viscosity, freezing point, and so on) to desired values (and or to meet regulatory requirements), it can be desirable to blend the middle distillate fraction with fossil fuel and/or with other renewable fuel (other than renewable fuel derived from HDO of a feedstock containing levulinic acid dimers/oligomers).

Particularly, the fuel may further contain fossil fuel, HEFA (hydroprocessed ester and fatty acids) fuel and/or HVO (hydrotreated vegetable oil) fuel.

The BOCLE lubricity of the renewable middle distillate composition may be 0.75 mm or less, preferably 0.72 mm or less, more preferably 0.70 mm or less, 0.69 mm or less, 0.68 mm or less, or 0.67 mm or less, as determined in accordance with ASTM D5001-10 (2014). One of the surprising findings of the present inventors is that the BOCLE lubricity of the middle distillate fraction, particularly of the aviation fuel fraction (LBAF; levulinic acid based aviation fuel fraction), is highly favourable, i.e. the middle distillate fraction achieves very low wear values.

Furthermore, a blend of LBAF and fossil aviation fuel can achieve even lower BOCLE values, in particular for blends containing 1.5 wt.-% LBAF or more, preferably 2.5 wt.-% LBAF or more, 3.0 wt.-% LBAF of more, or 4.0 wt.-% LBAF or more. The effect is well pronounced even if the content of LBAF in the blend is 40.0 wt.-% or less, preferably 30.0 wt.-% or less, 20.0 wt.-% or less, 15.0 wt.-% or less, 12.0 wt.-% or less or 10.0 wt.-% or less. Preferably, the BOCLE lubricity of the fuel of the present invention is 0.70 mm or less, preferably 0.67 mm or less, more preferably 0.66 mm or less, 0.65 mm or less, or 0.64 mm or less, as determined in accordance with ASTM D5001-10 (2014). Lubricity is a very important property in diesel fuels but also in military jet fuel use.

The present invention thus suitably provides an aviation fuel component having highly favourable BOCLE lubricity while at the same time allowing desirable swelling of seal/gasket elastomers and cleaner combustion due to low aromatics content.

Next a method for producing a middle distillate fraction is described. The middle distillate fraction contained in the fuel of the present invention is preferably produced by the method of the present invention. Further, the middle distillate fraction produced by the method preferably has the properties of the middle distillate fraction, as defined above for the middle distillate fraction contained in the fuel of the present invention.

The method for production of a renewable middle distillate composition comprises the steps of subjecting a feedstock comprising levulinic acid dimers/oligomers to at least one hydrodeoxygenation (HDO) reaction (HDO step), and fractionating (e.g. fractionated distillation) the resulting HDO product to obtain the middle distillate composition (fractionation step).

By employing levulinic acid dimers/oligomers, the middle distillate composition of the present invention is particularly suited as aviation and/or diesel fuel component. That is, the composition contains high an amount of paraffinic hydrocarbons (having high a content of cycloparaffins and isoparaffins) having 8 to 15 carbon atoms, wherein the majority (50% by weight or more) of the product has 9 or 10 carbon atoms.

Specifically, the method of the present invention provides products having a high content (usually more than 50%) of paraffinic hydrocarbons derived from levulinic acid dimers/oligomers, i.e. having 8 to 10 carbon atoms. Here, 10 is the total number of two levulinic acid carbon chains and the reduction by 1 to 2 carbon atoms takes account of carbon loss (e.g. decarboxylation) reactions occurring in a C—C-coupling step or in the HDO step. In this respect, a certain amount of higher molecular weight compounds (namely hydrocarbons derived from levulinic acid trimers) can be favourable in particular for fuel applications, since such a carbon number distribution mimics that of fossil oil fractions (fossil fuel).

Preferably, the middle distillate of the present invention has a boiling point range of 150° C. to 3700° C., more preferably 1500° C. to 285° C., 155 C to 260° C., or 180° C. to 285° C. The range below 285° C. is generally suitable as aviation fuel, which is preferred in the present invention, wherein the fraction boiling in the range of 155° C. to 260° C. is particularly preferable.

The levulinic acid dimers/oligomers may be obtained by dimerization/oligomerization of levulinic acid. Therefore, the method of the present invention may comprise a step of subjecting a raw material comprising at least levulinic acid to a C—C coupling reaction so as to produce the levulinic acid dimers/oligomers (C—C-coupling step). As said above, the levulinic acid may be in any form, such as free acid form, ester form or lactone form.

The C—C-coupling reaction may be conducted at a temperature in the range of 100-200° C., preferably 120-180° C., more preferably 120-160° C., most preferably 120-140° C., especially when the C—C coupling reaction is carried out in the presence of hydrogen and using an acidic ion exchange resin (IER). This temperature range was found to be particularly suitable for obtaining a high yield of levulinic acid dimers/oligomers which are suitable to be used in the feedstock.

It is to be noted that the upper limits and the lower limits of each range mentioned in the present description or claims may be combined to give new ranges which are intended to be comprised in the disclosure of the present invention.

In an embodiment, the present invention provides a method of producing the middle distillate fraction starting from levulinic acid. The method comprises the steps of providing a raw material comprising at least levulinic acid (preparation step), subjecting the raw material to a C—C coupling reaction so as to produce a C—C-coupling product containing levulinic acid dimers/oligomers (the above-mentioned C—C-coupling step), wherein the C—C coupling reaction is carried out in the presence of hydrogen and using an acidic ion exchange resin (IER) carrying a hydrogenating metal as a catalyst, subjecting a feedstock comprising at least the levulinic acid dimers/oligomers to a hydrodeoxygenation reaction to produce a HDO product (the above-mentioned HDO step), and fractionating the HDO product to obtain the middle distillate composition (the above-mentioned fractionation step).

This method is particularly preferable because it ensures that high an amount of levulinic acid dimers is produced in the C—C-coupling step in addition to a favourable amount of trimers and higher oligomers, so that the HDO step can be carried out without further purification/separation or with only minor purification/separation (such as removal of levulinic acid monomer, gaseous reaction products and/or water). However, the invention is not limited to this method and any method for producing the levulinic acid dimers/oligomers can be applied or the levulinic acid dimers/oligomers may be purchased. As the case may be, purification/separation of the levulinic acid dimers/oligomers (e.g. fractionation) may be desirable to achieve favourable contents of levulinic acid dimers/oligomers in the feedstock.

In the step of subjecting the feedstock to the C—C-coupling reaction, the levulinic acid undergoes a C—C-coupling reaction with another levulinic acid present in the feedstock so as to produce a levulinic acid dimer/oligomer.

Depending on the actual reaction conditions, the levulinic acid may undergo different C—C-coupling reactions. In particular the C—C-coupling reactions may be ketonisation reactions or reactions proceeding through an enol or enolate intermediate. Accordingly, the C—C-coupling reactions may be aldol-type reactions and condensations, ketonisations, reactions where the C—C-coupling involves an alkene, as well as other dimerization/oligomerization reactions. Further, decarboxylation, dehydration and/or hydrogenation may occur during or after the C—C-coupling reaction, thus providing a dimer/oligomer derivative having less oxygen and/or carbon atoms than expected from the C—C-coupling reaction alone.

Without wanting to be bound to theory, it is considered that an acidic IER (ion exchange resin) catalyst catalyses mainly aldol condensation reactions of levulinic acid. Under the reaction conditions of the C—C-coupling reaction, the resulting dimers/oligomers easily undergo lactonisation.

The hydrodeoxygenation (HDO) reaction may be carried out at any temperature, preferably at a temperature of at least 200° C., at least 250° C., at least 270° C., at least 290° C., at least 300° C., at least 305° C., or at least 310° C. A temperature of 280° C. or more in the HDO step leads to further (thermal) C—C-coupling reactions (further oligomerization reactions) in the HDO step.

Unless explicitly stated, the pressure values in the present invention relate to absolute pressures. Further, when speaking of hydrogen pressure or pressure of a specific gas in general, the partial pressure of hydrogen (or the specific gas) is meant.

Furthermore, levulinic acid dimers/oligomers in the feedstock may contain a keto group, an aldehyde group, an acid group (free acid form, ester form or lactone form) and/or a hydroxyl group.

In the present invention, it is to be noted that the term "feedstock" includes all non-gaseous material fed to the reactor, except for the material constituting the catalyst system. Thus, the calculation of the levulinic acid dimer/oligomer content in the feedstock does not consider the amount of catalyst. The same applies to the amounts of reactants fed in the HDO step or any other step of the methods of the present invention.

The method of the present invention may further comprise a step of removing unreacted levulinic acid and other monomers (separation step) before carrying out the HDO reaction.

Under practical reaction conditions, a dimerization/oligomerization reaction using an acidic IER catalyst system reaches a turnover of levulinic acid of about 50% by weight. Thus, about 50% by weight of the C—C-coupling reaction product consist of unreacted levulinic acid (monomer). This monomer is preferably removed before the HDO step. Most suitably, the monomer is removed immediately after the C—C-coupling reaction. Distillation is a suitable method for removing the monomer, but other methods may be employed as well. Specifically, the C—C-coupling reaction product may be fractionated to remove potential unreacted levulinic acid monomers and other light components such as water and $CO_2$ formed in the C—C-coupling. The unreacted levulinic acid (monomer) may be recycled and combined with the raw material.

The hydrogenation/hydrodeoxygenation reactions during levulinic acid condensation step may be carried out using a hydrogenating metal as a catalyst, wherein the hydrogenating metal is selected from metals of the Group VIII of the Periodic Table of Elements, preferably Co, Ni, Ru, Rh, Pd, and Pt, more preferably Pd, or a combination thereof.

These metals, in particular Pd, has been found to provide good hydrogenation properties and being well compatible with the requirements of the C—C-coupling reaction using an IER.

The present invention further relates to a use of a renewable middle distillate composition obtainable by hydrodeoxygenation of levulinic acid dimers/oligomers, followed by fractionated distillation, as an aviation fuel or aviation fuel component. When used as aviation fuel, the middle distillate fraction is prepared as an aviation fuel fraction, i.e. having a boiling point range in the aviation fuel range. The renewable middle distillate composition can be used as a diesel fuel or diesel fuel component as well, in particular as a winter diesel fuel component.

Preferably, the renewable middle distillate composition in accordance with the above-mentioned use is obtainable by the method of the present invention and/or has the properties as recited for the middle distillate fraction contained in the fuel of the present invention. In other words, it is preferable that the middle distillate compositions of the fuel, the method and the use of the present invention are the same.

Further aspects of the present invention are described in the following, while all of these aspects can be combined with the above-mentioned aspects without limitation.

In the method step employing hydrogen, the hydrogen may be mixed with one or more other gases (dilution gas), preferably an inert gas such as nitrogen, argon, helium or another of the noble gases, or gas behaving inertly to the reaction conditions of the present invention. By behaving inertly it is meant that the gas should not to a major extent participate as a reaction member, and preferably the inert gas should participate as little as possible, such as not participate at all.

While high a hydrogen pressure in the C—C-coupling step requires more sophisticated equipment, it is nevertheless possible to omit the mild hydrogenation step without needing to use long reaction times or highly reactive catalysts. Furthermore, a high hydrogen pressure in the C—C-coupling step was surprisingly found to shift the C—C-coupling reaction product (dimer/oligomer) from the lactone form to the diacid form. Since the lactone form dimers/oligomers tend to result in naphthenic or aromatic products after HDO, this embodiment is particularly suitable for the production of gasoline, Jet fuel components and chemical components.

The hydrogen pressure in this embodiment of the C—C-coupling step is preferably at least 35 bar, more preferably at least 40 bar, further preferably in the range of 45 to 55 bar. However, the upper hydrogen pressure is not necessarily limited and may be 200 bar or less, 100 bar or less, 80 bar or less, 70 bar or less, or 60 bar or less.

The C—C-coupling reaction can be controlled by adjusting several parameters, including by selection of reaction conditions such as weight hourly space velocity (WHSV) (kg feedstock/kg catalyst per hour).

The raw material may be obtained from processing of lignocellulosic material, and such processed material may be used directly, or purified to varying degrees before being used as a raw material in the method of the present invention. The levulinic acid may be produced e.g. with the Biofine method disclosed in U.S. Pat. No. 5,608,105.

Preferably, in the hydrodeoxygenation step, a HDO catalyst is employed which comprises a metal having hydrogenation catalyst function on a support, such as for example a HDO catalyst metal selected from a group consisting of Pd, Pt, Ni, Co, Mo, Ru, Rh, W or any combination of these. The metal having hydrogenation catalyst function may be carried on a support, preferably an inorganic oxide support, more preferably silica, alumina, titania, zirconia, carbon or a combination thereof. A highly preferable HDO catalyst comprises sulfided NiMo, which is preferably supported on an inorganic oxide such as alumina.

The hydrodeoxygenation step may be conducted at a temperature of up to 500° C. and at a pressure of 10-150 bar.

The method of the present invention may be carried out in a reactor, such as a stirred tank reactor, preferably a continuous stirred tank reactor, or a tubular flow reactor, preferably a continuous flow reactor. Further, the individual steps of the present invention may be carried out in the same reactor or in different reactors. Preferably, the C—C-coupling step and the HDO step are carried out in different reactors.

The product of the HDO step may optionally be subjected to an isomerization step in the presence of hydrogen and an isomerization catalyst. Both the HDO step and isomerisation step may be conducted in the same reactor. In some embodiments, the isomerisation catalyst is a noble metal bifunctional catalyst, for example Pt-SAPO or Pt-ZSM-catalyst. The isomerization step may for example be conducted at a temperature of 200-400° C. and at a pressure of 20-150 bar. Fractionation may be carried out before or after isomerization, but is preferably carried out after isomerization. Preferably, no isomerization treatment is carried out.

EXAMPLES

Example 1 (Production of Levulinic Acid Dimer)

A raw material containing 98 wt.-parts commercial grade levulinic acid (97 wt-% purity) and 2 wt.-parts water was provided. The raw material and hydrogen were fed to a tubular reactor supporting Amberlyst CH-34 catalyst (trade name; Pd doped ion exchange resin). The temperature in the reactor was adjusted to 130° C., the hydrogen pressure was 20 bar, WHSV was 0.2 h$^{-1}$ and hydrogen to raw material (liquid raw material) flow ratio was 1170 Nl/l.

The C—C-coupling product obtained after the tubular reactor contained 44 wt.-% non-reacted levulinic acid (LA) and γ-valerolactone (GVL), 53 wt.-% dimers and about 2 wt.-% oligomers. The non-reacted LA (+GVL) as well as light reaction products (e.g. $CO_2$) and water were separated by distillation.

The distilled product (C—C-coupling) had a LA dimer content of 95 wt.-%.

Example 2 (HDO of LA Dimer/Oligomer)

The product of Example 1 was subjected to HDO in a tubular reactor at a hydrogen pressure of 80 bar, a temperature of 306° C., and WHSV of 0.3 h$^{-1}$, using a sulfided NiMo hydrogenation catalyst supported on alumina and a flow rate of hydrogen to C—C-coupling of 2100 Nl/l.

The HDO product was fractionated and the composition of the thus obtained LBAF fraction (levulinic acid based aviation fuel fraction) (155-260° C.) was evaluated. The results are shown in Table 1, which further shows typical properties of fossil Jet A-1 fuel (by Neste), and HEFA component Jet fuel requirements (ASTM D7566 specification) and conventional Jet A1 requirements. The latter covers also Jet A1 fuel containing synthesized hydrocarbons (i.e. HEFA component).

The viscosity of the fuel is closely related to the pumpability over the temperature range and consistency of nozzle spray patterns. The main Jet fuel specifications allow a maximum viscosity (at −20° C.) of 8 mm$^2$/s. A maximum viscosity value of 12 mm$^2$/s at −40° C. is an operating limit provided by some of the aviation OEM's.

As can be seen, the test results comply with JET A-1 requirements, while the lubricity is even better than that of conventional fossil fuel. However, any new production route and component will anyways require ASTM certification.

Example 3 (Blends of LBAF and fossil fuel)

LBAF was prepared in the same manner as in Example 2. Blends of fossil Jet A-1 fuel (by Neste) and LBAF were tested for their freezing points and BOCLE lubricity. The results are shown in Table 2 and FIG. 1.

Example 4 (Blends of LBAF and NEXBTL Fuel)

LBAF was prepared in the same manner as in Example 2, except for using an aviation fuel fraction having a boiling point range of 180-285° C. Blends of NEXBTL jet fuel 1 (HEFA-SPK Jet A-1 fuel by Neste; produced in accordance with Example 1 of EP 2141217 B1) and LBAF were tested and the results are shown in Table 3.

Reference Example 5 (levulinic acid based diesel) LA based diesel was prepared in the same manner as in Example 2, except for using a diesel fuel fraction having a boiling point range of 180-360° C.

Test results are shown in Table 4.

TABLE 1

| Analysis | Test method | LBAF (Ex. 2) | ASTM D7566 A2 (HEFA component) | JET A-1 requirement | Neste Fossil JET A-1 (typical values) |
| --- | --- | --- | --- | --- | --- |
| Density, kg/m$^3$ | ASTM D4052 | 785.4 | 730-770 | 775-840 | 789.9 |
| viscosity −20° C., mm$^2$/s | ASTM D445 | 2.849 | — | max 8 | 2.828 |
| viscosity −40° C., mm$^2$/s | ASTM D445 | 5.056 | — | — | — |
| Freezing point, ° C. | IP 529 | <−80 *) | max −40 | max −47 | −68.7 |
| distillation ° C.: | ASTM D86 | | | | |
| 10 vol-% | | 164.9 | max 205 | max 205 | 163.6 |
| FBP | | 247.2 | max 300 | max 300 | 233.3 |
| residue, vol-% | | 1.3 | max 1.5 | max 1.5 | 1.3 |
| loss vol-% | | 0.6 | max 1.5 | max 1.5 | 0.6 |
| Existent gum, mg/100 ml | IP 540 | 5 | max 7 | max 7 | 1 |
| BOCLE lubricity, mm | ASTM D5001 | 0.67 | — | max 0.85 | 0.79 |
| HFRR lubricity µm/60° C. | ENISO12156-1 | 679 | — | — | — |
| Paraffins, wt.-% ASTM D2425 | | 30.0 | reported | | |

TABLE 1-continued

| Analysis | Test method | LBAF (Ex. 2) | ASTM D7566 A2 (HEFA component) | JET A-1 requirement | Neste Fossil JET A-1 (typical values) |
|---|---|---|---|---|---|
| Cycloparaffins/naphthenes wt.-% ASTM D2425 | | 67.4 | max 15 | | |
| Aromatics, wt.-% ASTM D2425 | | 2.6 | max 0.5 | | |
| Olefins, wt.-% ASTM D2425 | | <0.1 | | | |

*) Crystal not detected till −100° C.

TABLE 2

| LBAF Ex. 3 (rest in fossil) | BOCLE (mm) |
|---|---|
| 100 wt.-% | 0.67 |
| 70 wt.-% | — |
| 50 wt.-% | 0.67 |
| 30 wt.-% | 0.65 |
| 15 wt.-% | — |
| 10 wt.-% | 0.64 |
| 5 wt.-% | 0.63 |
| 1 wt.-% | 0.69 |
| 0 wt.-% | 0.71 |

TABLE 3

| Property | Method | NEXBTL jet | LBAF (Ex 3) | 80% NEXBTL jet 20% LBAF |
|---|---|---|---|---|
| Total aromatics, wt-% | EN12916, ASTM D2425 | <0.5 | 7.6 | 1.52 (calculated) |
| Monoaromatics, wt-% | EN12916 | N/A | 7.6 | |
| Di-aromatics, wt-% | EN12916 | N/A | <0.1 | |
| Tri+aromatics, wt-% | EN12916 | N/A | <0.1 | |
| Naphthenes, wt-% | ASTM D2425 | 0.88 | 61.1 | 12.92 (calculated) |
| Density, kg/m3 | ENISO12185, ASTM D4052 | 769.3 | N/A | 781.6 |
| Freezing point, ° C. | IP529 | −51.8 | N/A | −54.1 |
| Distillation | ASTM D7345, ASTM D86 | | N/A | |
| IBP | | N/A | N/A | 155.1 |
| 10% (T10) | | 185.8 | N/A | 185.4 |
| 50% (T50) | | 260.1 | N/A | 253.7 |
| 90% (T90) | | 281.4 | N/A | 282.7 |
| FBP | | 289.2 | N/A | 300.0 |
| residue | | 1.3 | N/A | 1.5 |
| loss | | 1.2 | N/A | 0.5 |
| T90-T10 | | 95.6 | N/A | 97.3 |

TABLE 4

| | Ex. 5 |
|---|---|
| COMPOSITION | |
| Aromatics | 11.8 wt-% |
| PROPERTIES | |
| Cetane Number | 47 |
| Density 15° C. | 854 kg/m³ |
| Cloud point | <−95° C. |
| Viscosity 40° C. | 3.6 mm²/s |
| Gross heating value | 45.9 MJ/kg |
| HFRR | 496 μm (micro-m) |
| TAN | <0.1 mg KOH/g |

The invention claimed is:

1. A fuel comprising:
a renewable middle distillate composition which includes a fractionally distilled hydrodeoxygenation product of a hydrodeoxygenated feedstock of dimers/oligomers of levulinic acid and/or dimers/oligomers of derivatives of levulinic acid, wherein the renewable middle distillate composition contains less than 10.0 wt.-% aromatics, as determined in accordance with ASTM D2425,
wherein the renewable middle distillate composition contains from 50 wt.-% to 80 wt.-% cycloparaffins having 8 to 15 carbon atoms, wherein 50 wt.-% or more of the cycloparaffins have 8 to 10 carbon atoms,
wherein the freezing point of the renewable middle distillate composition is −70° C. or lower, and
wherein the boiling point of the middle distillate composition is in the range of 150° C. to 370° C.

2. The fuel according to claim 1, wherein the renewable middle distillate composition contains at most 9.5 wt.-% of aromatics, as determined in accordance with ASTM D2425.

3. The fuel according to claim 1, wherein the fuel further contains fossil fuel, HEFA (hydroprocessed ester and fatty acids) fuel and/or HVO (hydrotreated vegetable oil) fuel.

4. The fuel according to claim 1, wherein the BOCLE lubricity of the renewable middle distillate composition is 0.75 mm or less, as determined in accordance with ASTM D5001-10 (2014).

5. The fuel according to claim 1, wherein the renewable middle distillate composition obtained by hydrodeoxygenation of dimers/oligomers of levulinic acid and/or dimers/oligomers of derivatives of levulinic acid followed by fractionated distillation, is an aviation fuel or aviation fuel component.

6. The fuel according to claim 1, wherein the renewable middle distillate composition contains at most 3.0 wt.-% of aromatics, as determined in accordance with ASTM D2425.

7. The fuel according to claim 2, wherein the freezing point of the renewable middle distillate composition is −95 C or lower.

8. The fuel according to claim 2, wherein the renewable middle distillate composition contains at least 55 wt.-% of cycloparaffins, as determined in accordance with ASTM D2425.

9. The fuel according to claim 2, wherein the renewable middle distillate composition contains at most 70 wt.-% of cycloparaffins, as determined in accordance with ASTM D2425.

10. The fuel according to claim 2, wherein the BOCLE lubricity of the renewable middle distillate composition is 0.67 mm or less, as determined in accordance with ASTM D5001-10 (2014).

* * * * *